United States Patent [19]

Artiss et al.

[11] Patent Number: 5,116,730

[45] Date of Patent: May 26, 1992

[54] AMINO ACID SUBSTITUTED 4-AMINOPHENAZONES FOR MEASURING ENZYME ACTIVITY

[75] Inventors: Joseph D. Artiss, Windsor, Ontario, Canada; Jill M. Bensie, Ferndale; Bennie Zak, West Bloomfield, both of Mich.; Daniel S. Raden, Hawthorn Woods, Ill.

[73] Assignee: Board of Governors of Wayne State University, Detroit, Mich.

[21] Appl. No.: 206,835

[22] Filed: Jun. 15, 1988

[51] Int. Cl.$^5$ .................... C12Q 1/48; C12Q 1/37; C12Q 1/26

[52] U.S. Cl. ...................................... 435/15; 435/24; 435/25; 435/810

[58] Field of Search ............... 548/358, 365, 366; 435/4, 15, 25, 24

[56] References Cited

U.S. PATENT DOCUMENTS

| | | | |
|---|---|---|---|
| 4,281,181 | 7/1981 | Nagasawa et al. | 562/453 |
| 4,511,651 | 4/1985 | Beaty et al. | 435/15 |
| 4,529,709 | 7/1985 | Takabayashi et al. | 435/24 |
| 4,567,138 | 1/1986 | Beck et al. | 435/15 |
| 4,588,836 | 5/1986 | Matsumoto et al. | 562/448 |
| 4,751,178 | 6/1988 | Babb et al. | 435/15 |

OTHER PUBLICATIONS

Jeske et al., Chem. Abs. 87:145661x, 1977.
Moss, D. W. et al., Enzymes, In:Teitz, N. W., ed. Textbook of Clinical Chemistry, Philadelphia:W. G. Saunders, 5:721-722, (1986).
Hanes, C. S., et al., Biochem. J. 51:25-35 (1952).
Goldbarg, J. et al., Arch. Biochem. Biophys. 91:61-70 (1960).
Orlowski, M., et al., Clin. Chem. Acta 7:775-760 (1962).
Fossati, P., et al., Clin Chem., 32:1581-1584 (1986).
Artiss, J., et al., Microchemical Journal 26:487-505 (1981).
Szasz, G., Clin. Chem. 15:124-136 (1969).
Tamaoku, K., et al., Anal. Chim. Acta, Elsevier Scientific Publishing Company, 136:121-127 (1982).
Tamaoku, K., et al., Chem. Pharm. Bull., 30:2492-2497 (1982).
Meth. Enzymol. 19:789-797 (1970).
J. Chem. Soc., 24:3315-3319 (1949).
J. Chem. Soc., 32:886-894 (1957).
J. Amer. Chem. Soc., 72:2469-2474 (1950).
Shaw et al., Clin. Chem. 23:79-85 (1977).

*Primary Examiner*—Esther L. Kepplinger
*Assistant Examiner*—Donna C. Wortman
*Attorney, Agent, or Firm*—Ian C. McLeod

[57] ABSTRACT

Novel substrates which are amino acid 4-amino phenazones for detecting enzymes, particularly L-gamma-glutamyltransferase, are described. The amino acid gamma-glutamyl-4-aminophenazone reacts with the enzyme to produce 4-aminophenazone which is an amino dye intermediate. The amino dye intermediate is coupled with a second dye intermediate to form a chromogen. The 4-aminophenazone is particularly reacted with a phenolic naphtholic or aniline compound, particularly the phenolic compound 2-hydroxy-3,5-dichlorobenzenesulfonate, to form a red chromogen in the presence of an oxidizing agent, such as bilirubin oxidase.

18 Claims, No Drawings

AMINO ACID SUBSTITUTED 4-AMINOPHENAZONES FOR MEASURING ENZYME ACTIVITY

BACKGROUND OF THE INVENTION (1) Summary of the Invention

The present invention relates to novel amides which are amino acid substituted 4-aminophenazones used as substrates for measuring enzyme activity. In particular the present invention relates to amino acid substituted 4-aminophenazones, particularly glutamyl-4-aminophenazones, wherein the amino acid substituent is cleaved by the enzyme which recognizes the amino acid to produce 4-aminophenazone which is then used as an amine dye intermediate which is reacted with a second dye intermediate in the presence of an oxidizing agent to produce a chromogen.

(2) Prior Art

Serum Gamma glutamyltransferase (GGT) is elevated in all liver diseases (Moss, D. W., et al. Enzymes. In: Teitz, N. W., ed. Textbook of Clinical Chemistry. Philadelphia: W. B. Saunders, 5:721-722 (1986)). For the detection of obstructive jaundice, cholangitis, and cholecystitis, it is more sensitive than alkaline phosphatase, 5'-nucleotidase, leucine aminopeptidase, and the transaminases (Moss, D. W., et al. Enzymes. In: Teitz, N. W., ed. Textbook of Clinical Chemistry. Philadelphia: W. B. Saunders, 5:721-722 (1986)). Its rise occurs earlier than with these other enzymes and persists longer. The measurement of serum GGT activities is very valuable in the detection of alcohol-induced liver diseases. Not only are elevated levels of GGT found in the sera of patients with alcoholic cirrhosis, but also in the majority of sera from persons who are heavy drinkers (Moss, D. W., et al. Enzymes. In: Teitz, N. W., ed. Textbook of Clinical Chemistry. Philadelphia: W. B. Saunders, 5:721-722 (1986)).

The first methods for GGT measurement involved the use of the physiological substrate glutathione (Hanes, C. S., et al. Biochem. J. 51:25-35(1952); but these were cumbersome and quickly replaced by methods using synthetic substrates. The use of synthetic substrates such as N-(DL-gamma-glutamyl)aniline (Goldbarg, J., et al., Arch. Biochem. Biophys. 91:61-70 (1960)), L-gamma-glutamyl-naphthylamide (Orlowski, M., et al., Clin. Chem. Acta 7:755-760 (1962), and L-gamma-glutamyl-p-nitroanilide (Szasz, G., Clin. Chem. 15:124-136 (1969)) all involve production of dyes from cleavage products, but have definite limitations for routine use. See also U.S. Pat. Nos. 4,511,651 to Beaty et al and 4,567,138 to Beck et al.

At present, the substrate of choice for measurement of GGT activity is L-gamma-glutamyl-3-carboxy-4-nitroanilide (gluCANA) (IFCC Methods for the Measurement of Catalytic Concentration of Enzymes, Part 4, IFCC Method for gamma-Glutamyltransferase [(gamma-Glutamyl)-Peptide: Amino Acid gamma-Glutamyltransferase, EC 2.3.2.2], 1983). Its high turn-over rate and solubility give it a distinct advantage over its predecesser, L-gamma-glutamyl-p-nitroanilide (gluPA), which suffers from poor solubility. But both substrates have a low molar absorptivity, and both exhibit overlapping spectra of substrate and product, causing measurement to be performed on the spectrum shoulder rather than at the dye's absorption peak (Fossati, P., et al. Clin. Chem., 32:1581-1584 (1986)).

OBJECTS

It is therefore an object of the present invention to provide novel amides which are amino acid substituted-4-aminophenazones which are useful as substrates for enzymes to produce 4-aminophenazone which is a dye intermediate. Further it is an object of the present invention to provide a method for assaying for enzymes and a test kit for the use of the novel amino acid 4-aminophenazones. Further still, it is an object of the present invention to provide an assay method and test kit which is relatively inexpensive and very reliable. These and other objects will become increasingly apparent by reference to the following description.

GENERAL DESCRIPTION

The present invention relates to a compound of the formula:

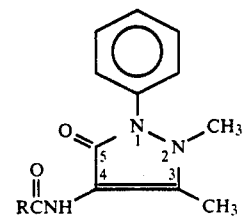

wherein

is an amino acid group containing between 2 and 6 carbon atoms.

Further the present invention relates to an improvement in the method for detecting an enzyme by providing an amino acid coupled to a heterocyclic ring compound which reacts with the enzyme to form a heterocyclic amine dye intermediate which is then coupled with a second dye intermediate to form a chromogen the improvement which comprises:

(a) providing a compound of the formula:

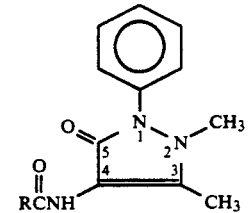

wherein

is an amino acid group containing between 2 and 6 carbon atoms in an aqueous solution with an acceptor for amino acid carbonyl group produced by the reaction with the enzyme;

(b) reacting the compound with the enzyme to form a 4-amino dye intermediate of the formula:

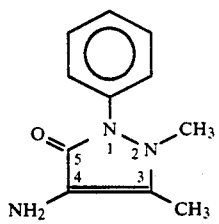

and the amino acid carbonyl group reacted with the acceptor; and (c) coupling the 4-amino dye intermediate with a second dye intermediate in the presence of an oxidizing agent to form a chromogen dye complex which is a reaction product of the 4-amino group of the 4-amino dye intermediate with the second dye intermediate.

Further still the present invention relates to a method for detecting glutamyltransferase which comprises:

(a) providing 1-phenyl-2-methyl-3-methyl-4-glutamylamino-3-pyrazolin-5-one in an aqueous solution with an acceptor for a glutamyl carboxy group produced by a reaction of the enzyme with the glutamyl group;

(b) providing the glutamyltransferase in the solution to produce 1-phenyl-2-methyl-3-methyl-4-amino-3-pyrazoline-5-one in the solution as an amino dye intermediate and a reaction product of the acceptor with the glutamyl carboxy group;

(c) reacting the 1-phenyl-2-methyl-3-methyl-4-amino-3-pyrazoline-5-one with an oxidizing agent and a second dye intermediate to form a dye complex which is a reaction product of the 4-amino group of the amino dye intermediate and the second dye intermediate.

Finally the present invention relates to a test kit for determining the presence of an enzyme which cleaves an amino acid to form an amino dye intermediate, wherein the amino dye intermediate is reacted with a second dye intermediate in the presence of an oxidizing agent to form a chromogen which comprises providing in the test kit (a) a compound of the formula:

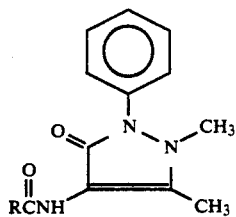

wherein

is an amino acid group containing between 2 and 6 carbon atoms, with the enzyme to form a 4-amino dye intermediate; and (b) a second dye intermediate which reacts with the 4-amino dye intermediate to form a chromogen dye complex and (c) an oxidizing agent which produces the reaction between the 4-amino group of the 4-amino dye intermediate and the second dye intermediate to produce the chromogen dye complex; and (d) an acceptor for an amino acid carbonyl group released by the reaction with the enzyme.

The compounds of the present invention can be referred to as amino acid-4-phenazonylamides or N-(amino acid)-phenazonylamides. The preferred compound can be referred to as 4-glutamyl phenazone amide. It can also be referred to as glutamyl-4-phenazonylamide or N-(glutamyl)-phenazonylamide. The glutamyl group is preferably the L-gamma-isomer which is recognized by gamma-glutamyltransferase.

The amino acid 4-aminophenazone amide reacts with a transferase to produce 4-aminophenazone which is an amine dye intermediate which reacts with a second dye intermediate to form a chromogen dye complex in the presence of an oxidizing agent. Preferably this chromogen dye complex is a 4-monoimino derivative of the 4-aminophenazone produced by a reaction with a phenol. The chromogen dye complex could also be an azo derivative produced by reacting a second dye intermediate containing an amino group. The 4-amino acid phenazone amide compounds are essentially colorless in solution and thus do not interfere with the measurement of the chromogen dye complex since all of the color is developed by the complex.

Thus glutamyl 4-aminophenazone reacts with gamma glutamyltransferase (GGT) to produce 4-aminophenazone as an amine dye intermediate which in turn reacts with a second dye forming intermediate, such as 2-hydroxy-3,5-dichlorobenzenesulfonate (HDCBS), in the presence of an oxidizing agent, such as bilirubin oxidase, (BOX) to form a chromogen dye complex, particularly a red color with the specific reagents. Essentially any strong oxidizing agent, such as potassium ferricyanide can be used to facilitate the reaction for formation of the chromogen dye complex.

Phenolic compounds are preferred, second dye forming intermediates, and examples are 2-hydroxy-3,5-dichlorobenzenesulfonate; 2,5-dimethyl phenol; and in general phenols, naphthols and their derivatives. Oxidases as oxidizing agents are for instance bilirubin oxidase, ascorbate oxidase, laccase and peroxidase or microperoxidase with hydrogen peroxide or an organic peroxide. Chemical oxidizing agents are for instance potassium ferricyanide. Intermediates for forming azo dye complexes are for instance N-ethyl-N-(2-hydroxy-3-sulfonopryl)-m-toluidine; N-ethyl-N-sulfopropylaniline; or N-sulfopropylaniline. The formation of various chromogen dye complexes using aminoheterocyclic compounds is well known to those skilled in the art and is described by Artiss et al in Microchemical Journal 26, 487–505 (1981). Trinder's Reagents as described in K. Tamaoku, et al Anal. Chim. Acta, 136, 121(1982) and Chem. Pharm. Bull., 30, 2492 (1982) can be used.

Acceptors are for instance glycylglycine (gly) which reacts with the carbonyl group cleaved from the amide group of the 4-amino acid phenazone. Other acceptors are for instance glycylglycylglycine or water.

The enzymes which can be detected are: L-gamma glutamyltransferase, alanine aminopeptidase, glycyl transpeptidase and the like. The amino acid is picked to match the enzyme.

The compounds of the present invention are represented by the structural formula:

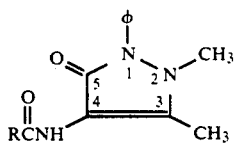

wherein φ is phenyl and wherein

is an amino acid group. Preferably

is a glutamyl group and the compound can be trivially referred to as glutamyl-4-aminophenazone or more accurately 1-phenyl-2-methyl-3-methyl-4-glutamylamino-3-pyrazolin-5-one. Another preferred

group is alaninyl

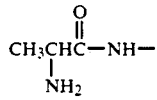

or glycyl

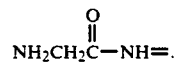

To prepare the amino acid -4-aminophenazone, glutamic acid (or other amino acid) with both alpha-functional groups masked, e.g. N-t-BOC-L-glutamic acid alpha-benzyl ester (where t-BOC is t-butyloxycarbonyl), can be reacted with 4-aminophenazone in the presence of dicyclohexylcarbodiimide (DCC) and a solvent (such as dioxane or tetrahydrofuran) first at 0°, then at room temperature. The desired alpha-masked product can be purified from the reaction mixture and then subjected to trifluoroacetic acid in methylene chloride, to remove the BOC group, and to hydrogenolysis, to remove the alpha-benzyl group, thereby liberating glutamyl-4-aminophenazone. The reactions are as follows:

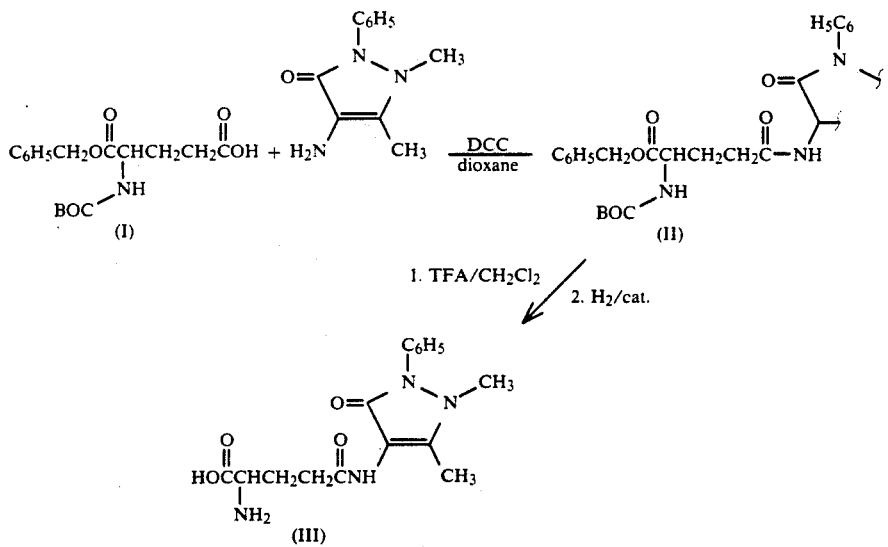

A possible alternate synthesis is

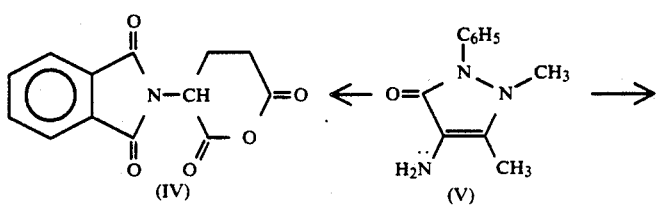

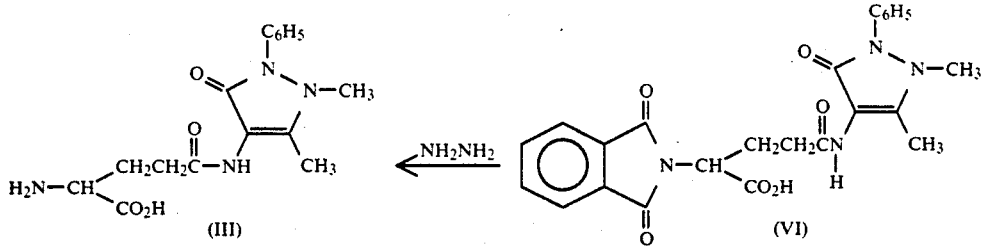

by analogy with: Meth. Enzymol 19:789–797 (1970); J. Chem. Soc. 3315 (1949); J. Amer. Chem. Soc. 72:2469 (1950); and to J. Chem. Soc. 886 (1957) for synthesis of starting anhydride and for conditions of gamma-amide bond formation and of subsequent de-phthaloylation using hydrazine hydrate.

The compound glutamyl-4-aminophenazone could also be prepared by reacting L-gamma-glutamic acid methyl ester with 4-aminophenazone in the presence of a base in a solvent (chloroform). The compound must be purified for use to eliminate residual amine.

The following is a description of the preferred process for producing glutamyl-4-aminophenazone:

Step 1a

A solution of N-(t-BOC)-glutamic acid-α-benzylester (33.7 parts by weight "pbw") and triethylamine (10.1 pbw) in chloroform was cooled to 0° C. and stirred; isobutyl chloroformate (13.7 pbw) was added dropwise. The bath was removed and the reaction mixture was stirred for 16 hours. At this point, 4-aminoantipyrene (20.3 pbw) was added portionwise and the reaction mixture was stirred overnight at ambient temperature. The reaction mixture was stripped in vacuo. The residue was triturated with ethyl acetate and filtered. The filtrate was stripped in vacuo, leaving a glassy residue. NMR & MS analysis confirm the expected structure. Yield of crude product is essentially quantitative.

Step 1b

To a chilled (0° C.) solution of N-CBZ-glutamic acid-α-benzyl ester (50 pbw) and triethylamine (15 pbw) in chloroform was added, dropwise, isobutyl chloroformate (20.3 pbw). The reaction mixture was stirred overnight at ambient temperatures. The reaction mixture was stripped in vacuo and the slushy residue was stirred with ethyl acetate. The mixture was filtered and the filtercake washed with ethyl acetate. The organic filtrate was washed with dilute HCl, water, dilute aqueous sodium bicarbonate and water, then dried over anhydrous magnesium sulfate. After filtering off the drying agent, the organic solution was stripped in vacuo, yielding an orange-red viscous oil in 97% yield. Analytical thin-layer-chromatography shows several minor impurities (silica gel, 2% ethanol in ethyl acetate). The material was purified by flash chromatography on silica gel (3% ethanol in ethyl acetate). The product was obtained as a lemon yellow solid. Structural confirmation was obtained by NMR and MS analyses.

Step 2a: Debenzylation

To a solution of N-(t-BOC)-4-(γ-glutamylamido)-antipyrene-α-benzyl ester (42.2 pbw) in dimethyl formamide was added ammonium formate (30.0 pbw). This mixture was stirred while adding 10% palladium on carbon (30.0 pbw). Stirring was continued until no starting material was noted on TLC (silica gel, 3% methanol in ethyl acetate). This required about one hour. The reaction mixture was filtered with suction through a short pad of Celite ®. The filtrate was subjected to high vacuum to remove most of the dimethyl formamide. The residue was taken up in ethyl acetate, washed with saturated brine and dried over anhydrous magnesium sulfate. The organic solution was filtered and the filtrate stripped in vacuo to yield an off-white, viscous oil; yield of crude material, 98%. NMR and MS analyses confirm the structure.

Step 3a: Removal of BOC-group, preparation of desired 4-(γ-glutamylamido) antipyrene To a solution of N-(t-BOC)-4-(γ-glutamylamido)-antipyrene (21.6 pbw) in dry acetonitrile, under nitrogen, was added sodium iodide (22.5 pbw). The mixture was stirred at ambient temperature until a clear solution was obtained. To this solution was added trimethylsilyl chloride (10.8 pbw) in one portion. Stirring was continued until no starting material remained by TLC (silica gel, 10% methanol in ethyl acetate containing 1% acetic acid), about 2 hours. Methanol was added to the reaction mixture, stirred for 15 minutes then placed in a refrigerator overnight. The reaction mixture was stripped in vacuo and the residue partitioned between ether and 30% aqueous acetic acid. The aqueous phase was washed with additional ether, then decolorized by adding a few crystals of sodium bisulfite. The solution was run through a bed of Amberlite ® XAD-2 resin (Rohm & Haas Co.), eluting first with distilled water, then with 1:1 ethanol: distilled water. The aqueous ethanolic solution was stripped in vacuo to yield the desired product as a pale yellow glass. Structure is confirmed by NMR and MS analyses.

Step 2b: Deprotection of N-CBZ-4-(γ-glutamylamido)-antipyrene

A solution of N-CBZ-4 (γ-glutamylamido)-antipyrene-α-benzylester in absolute ethanol was treated with hydrogen gas under 3 atm. pressure in the presence of 10% Pd on carbon as catalyst. When the theoretical uptake of hydrogen had been noted, thin layer chromatography (silica gel, 10% methanol in ethyl acetate containing 1% acetic acid) showed no trace of starting material and one spot, having the same Rf as the material obtained in Step 3a (supra). The reaction mixture was filtered, with suction, through a short pad of Celite ®. The filtrate was stripped in vacuo. The residue, the desired 4-(γ-glutamylamido)-antipyrene, was obtained as an off-white solid. Confirmation of structure was obtained by NMR and mass spectrometry. Identity of this material with that obtained in Step 3a was shown by high performance liquid chromatography (HPLC), running the samples individually and by co-injection.

The reactions are as follows:

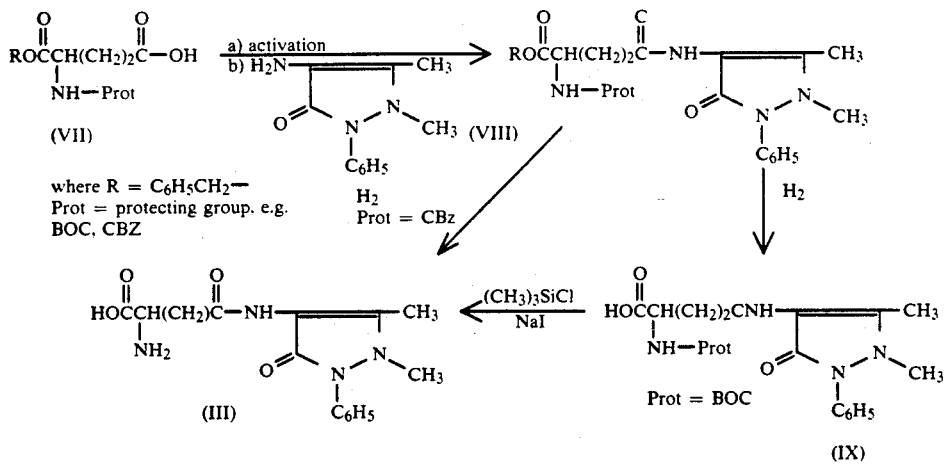

SPECIFIC DESCRIPTION

The following Example 1 shows a kinetic assay of gamma-glutamyltransferase using the donor substrate, 4-glutamylphenazone. The kinetic colorimetric method for measuring gamma-glutamyltransferase (GGT) activity in serum uses the new donor substrate, L-gamma-glutamyl-4-aminophenazone (L-gamma-glutamyl-4-aminoantipyrene) (gAAP), with glycylglycine (gly) as the acceptor for the cleaved carbonyl moiety. 2-hydroxy-3,5-dichlorobenzenesulfonate (HDCBS), in the presence of bilirubin oxidase (BOX), reacts with the released product, 4-aminoantipyrene (4AAP), to produce a red dye complex. The peak absorption for the dye complex is at 510nm. The donor substrate shows no absorption throughout the visible spectrum. The reaction takes place in a single cuvet, with all reagents in a single working solution. The method is adaptable to automation.

The method takes advantage of a colorless donor substrate forming a colored product. The GGT transfers the gamma-glutamyl derived carbonyl group from gAAP to glycylglycine. The 4-aminoantipyrene is released and couples with the HDCBS in the presence of the BOX to form the red dye complex. The reaction is monitored kinetically, with the change in absorbance per minute proportional to the activity of GGT present in the sample. BOX can be replaced by other enzymes, such as laccase or ascorbate oxidase, that exhibit peroxidase-like activity or by peroxidase or microperoxidase itself in the presence of hydrogen peroxide or an organic peroxide.

MATERIALS and METHODS

Apparatus—A UV-260 double-beam spectrophotometer with a temperature-controlled cuvet holder (Shimadzu, Kyoto, Japan) was used.

Materials—BOX, purchased from Amano International Enzyme Co., Troy, Va. One unit of BOX is defined as the amount of enzyme that oxidizes 1 μmol of bilirubin per minute at pH 7.0 and 37° C. HDCBS, obtained from Biosynth AG, Zurich, Switzerland. Bovine GGT, glycylglycine and Triton X-100, purchased from Sigma Chemical Co., St. Louis, Mo. Tris(hydroxymethyl)aminomethane, purchased from Fisher Scientific Co., Fair Lawn, N.J.

Reagents—The single reagent contains, per liter, 5000 U BOX, 20.0 mmol gAAP, 13.0 mmol HDCBS, 5.0 mmol glycylglycine, and 15 g Triton X-100 in 50 mmol/liter Tris-HCl buffer, pH 7.9. GGT standards are also made up in Tris-HCl buffer, 50 mmol/L, pH 7.9.

Procedure—Add 10 microliters GGT standard to 1.0 ml reagent. Record the change in absorbance at 510 nm and 37° C. for 180 seconds after a 120 second lag phase. The reaction is run vs. a reagent blank.

Calculation of Activity Activity U/L $=(\Delta A/min) \times$ Factor where Factor $=$(total vol (ml)/sample vol (ml))$\times$(mol/micromol)/molar absorptivity.

$=(1.01/0.01)\times(10^6/26,000)=3885$

RESULTS

Concentrations of Constituents—The reaction was optimized to contain 13.0 mmol HDCBS, 5.0 mmol glycylglycine, 20.0 mmol gAAP, and 5000 U BOX per liter of buffer to yield the maximum GGT activity in the reaction mixture.

Molar Absorptivity of Dye—The molar absorptivity of the red dye complex was measured by adding increments of 4AAP in place of gAAP to quantitatively generate different concentrations of the dye to give absorbance values between 0.100 and 1.000. The molar absorptivity of the dye at 510 nm was calculated to be 26,000 L mol$^{-1}$ cm$^{-1}$.

Km Value of GGT—The Km value for bovine kidney GGT was determined for gAAP by linear regression with a Lineweaver-Burk plot. The Km for GGT was calculated to be about 9.9 mmol/liter as compared to 6.3 and 6.8 mmol/liter for fractions A and B of the purified enzyme, respectively, with N-(gamma-L-glutamyl-alpha-naphthylamide as the substrate (Szewezick, A., et al. Biochemische Zeitschrift, 338, 317–329 (1963)). Another source found the Km and V$_{max}$ for bovine kidney GGT to be 0.98 mmol/liter and 177 micromol/min/mg, respectively, with gamma glutamyl-p-nitroanilide as substrate (Allen, L. M., et al., Chem.-Biol. Interactions 33, 361–365 (1981). Our V$_{max}$ was calculated to be 36.8 micromol/min/milligram.

Absorption Spectra—The absorption maximum of the product is 510 nm. The donor substrate shows no absorption throughout the visible spectrum.

Course of the Reaction—The rate of the GGT reaction at 37° C. and 510 nm became linear after about 2 minutes.

DISCUSSION

The present invention utilizes a new, colorless donor substrate, gAAP, which forms a red colored product with a high molar absorptivity. There is no overlapping of substrate and product spectra, as with the methods using gluCANA or gluPA, and sample size is reduced 10-fold (from 100 microl to 10 microl).

The excellent solubility of the substrate, its spectral characteristics, increased sensitivity and adaptability to automation make this method a preferred alternative to current methods using glu-CANA or gluPA.

As with the prior art, this procedure is useful for the determination of gamma-glutamyltransferase activity in blood serum. Upon removal of the red cells an appropriate aliquot of the serum is contacted with the reagent. The removal of the red cells is by centrifugation or filtration.

It is intended that the foregoing description be only illustrative and that the present invention be limited only by the hereinafter appended claims.

I claim:

1. In a method for detecting an enzyme by providing an amino acid coupled to an amino dye intermediate wherein the amino acid is cleaved by the enzyme to form the dye intermediate which is then coupled with a second dye intermediate to form a chromogen the improvement which comprises:
   (a) providing a compound of the formula:

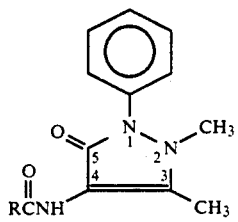

wherein

is an amino acid group recognized by the enzyme and containing between 2 and 6 carbon atoms in an aqueous solution with an acceptor for an amino acid carbonyl group produced by the reaction with the enzyme;
   (b) reacting the compound with the enzyme to form a 4-amino dye intermediate of the formula:

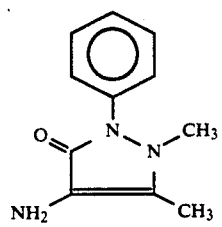

and the amino acid carbonyl group reacted with the acceptor; and
   (c) coupling the 4-amino dye intermediate with a second dye intermediate in the presence of an oxidizing agent to form a chromogen dye complex which is a reaction product of the 4-amino group of the 4-amino dye intermediate with the second dye intermediate.

2. The method of claim 1 wherein

is alaninyl and wherein the enzyme is alanine aminopeptidase.

3. The method of claim 1 wherein

is glutamyl and wherein the enzyme is glutamyl transferase.

4. The method of claim 1 wherein

is glycyl and wherein the enzyme is glycyl transpeptidase.

5. The method of claim 1 wherein the second dye intermediate is an aniline, naphthol or phenolic compound and wherein the chromogen dye complex is a 4-monoimino derivative of the compound.

6. The method of claim 1 wherein the second dye intermediate is 2-hydroxy-3,5-dichlorobenzenesulfonate.

7. A method for detecting glutamyltransferase which comprises:
   (a) providing 1-phenyl-2-N-methyl-3-methyl-4-glutamylamino-3-pyrazolin-5-one in an aqueous solution wit an acceptor for a glutamyl carboxy group produced by a reaction of the enzyme with the glutamyl group;
   (b) providing the glutamyltransferase in the solution to produce 1-phenyl-2-N-methyl-3-methyl-4-amino-3-pyrazoline-5-one in the solution as an amino dye intermediate and a reaction product of the acceptor with the glutamyl carboxy group;
   (c) reacting the 1-phenyl-2-N-methyl-3-methyl-4-amino-3-pyrazoline-5-one with an oxidizing agent and a second dye intermediate to form a dye complex which is a reaction product of the 4-amino group of the amino dye intermediate and the second dye intermediate.

8. The method of claim 7 wherein the dye intermediate is 2-hydroxy-3,5-dichlorobenzenesulfonate.

9. The method of claim 8 wherein the oxidizing agent is an oxidase enzyme.

10. The method of claim 9 wherein the oxidase enzyme is bilirubin oxidase.

11. The method of claim 8 wherein the oxidizing agent is potassium ferricyanide.

12. A test kit for determining the presence of an enzyme which cleaves an amino acid to form an amino dye intermediate and wherein the amino dye intermediate is reacted with a second dye intermediate in the presence of an oxidizing agent to form a chromogen which comprises:

(a) a compound of the formula:

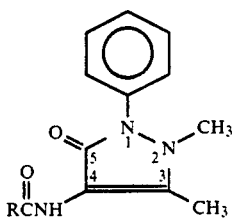

which reacts with the enzyme to form a compound of the formula

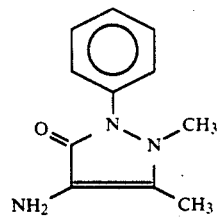

as a 4-amino dye intermediate; and (b) a second dye intermediate which reacts with the 4-amino dye intermediate to form a chromogen dye complex;

(c) an oxidizing agent which produces the reaction between the 4-amino group of the 4-amino dye intermediate and the second dye intermediate to produce the chromogen dye complex; and (d) an acceptor for an amino acid carbonyl group released by the reaction with the enzyme.

13. The test kit of claim 12 wherein R is a glutamyl group.

14. The test kit of claim 13 wherein the second dye intermediate is a phenolic compound and wherein the chromogen dye complex is a 4-monoimino compound.

15. The test kit of claim 14 wherein the phenolic compound is 2-hydroxy-3,5-dichlorobenzenesulfonate.

16. The test kit of claim 15 wherein the oxidizing agent is an oxidase enzyme.

17. The test kit of claim 16 wherein the oxidase enzyme is bilirubin oxidase.

18. The test kit of claim 12 wherein the oxidizing agent is potassium ferricyanide.

* * * * *

UNITED STATES PATENT AND TRADEMARK OFFICE
CERTIFICATE OF CORRECTION

PATENT NO. : 5,116,730
DATED : May 26, 1992
INVENTOR(S) : Joseph D. Artiss, Jill M. Bensie, Bennie Zak and Daniel S. Raden It is certified that error appears in the above—identified patent and that said Letters Patent is hereby corrected as shown below:

Columns 5 and 6, last reaction: 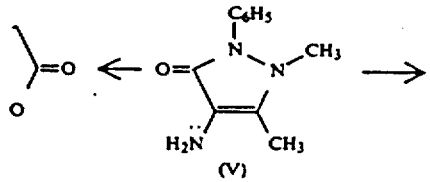

should be 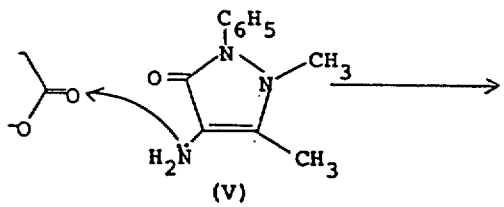

Column 12, line 43, "wit" should be --with--.

Signed and Sealed this

Twentieth Day of July, 1993

Attest:

MICHAEL K. KIRK

Attesting Officer         Acting Commissioner of Patents and Trademarks